(12) United States Patent
George

(10) Patent No.: US 8,979,751 B2
(45) Date of Patent: Mar. 17, 2015

(54) SPECULA

(76) Inventor: Samuel George, Weybridge (GB)

(*) Notice: Subject to any disclaimer, the term of this patent is extended or adjusted under 35 U.S.C. 154(b) by 1289 days.

(21) Appl. No.: 11/793,164

(22) PCT Filed: Dec. 15, 2005

(86) PCT No.: PCT/GB2005/004858
§ 371 (c)(1),
(2), (4) Date: Apr. 3, 2008

(87) PCT Pub. No.: WO2006/064247
PCT Pub. Date: Jun. 22, 2006

(65) Prior Publication Data
US 2009/0099422 A1 Apr. 16, 2009

(30) Foreign Application Priority Data

Dec. 15, 2004 (GB) .................................. 0427506.1
Aug. 22, 2005 (GB) .................................. 0517103.8

(51) Int. Cl.
*A61B 1/32* (2006.01)
*A61B 17/02* (2006.01)
*A61B 17/28* (2006.01)

(52) U.S. Cl.
CPC ............... *A61B 1/32* (2013.01); *A61B 17/0206* (2013.01); *A61B 2017/2837* (2013.01)
USPC ............................ 600/224; 600/214; 600/215

(58) Field of Classification Search
USPC .................................................. 600/184–246
See application file for complete search history.

(56) References Cited

U.S. PATENT DOCUMENTS

| 55,511 | A | * | 6/1866 | Lentz | 600/224 |
| 3,575,163 | A | * | 4/1971 | Gasper | 600/222 |
| 3,890,961 | A | * | 6/1975 | Moore et al. | 600/222 |
| 5,007,409 | A | * | 4/1991 | Pope | 600/203 |
| 5,174,278 | A | * | 12/1992 | Babkow | 600/210 |
| 5,509,893 | A | * | 4/1996 | Pracas | 600/224 |
| 6,024,696 | A | | 2/2000 | Hoftman et al. | |
| 6,048,308 | A | | 4/2000 | Strong | |
| 6,096,046 | A | * | 8/2000 | Weiss | 606/119 |
| 6,379,299 | B1 | * | 4/2002 | Borodulin et al. | 600/220 |
| 6,416,467 | B1 | * | 7/2002 | McMillin et al. | 600/224 |
| 2002/0016528 | A1 | * | 2/2002 | Tan | 600/224 |
| 2002/0022771 | A1 | * | 2/2002 | Diokno et al. | 600/220 |
| 2002/0177791 | A1 | * | 11/2002 | Diokno et al. | 600/591 |

FOREIGN PATENT DOCUMENTS

| GB | WO0069325 | * 11/2000 | ............... A61B 1/32 |
| WO | WO 92/21279 A1 | 12/1992 | |
| WO | WO 98/11818 A1 | 3/1998 | |
| WO | WO 99/12466 A1 | 3/1999 | |
| WO | WO 00/69325 A1 | 11/2000 | |
| WO | WO 01/89407 A2 | 11/2001 | |

* cited by examiner

*Primary Examiner* — Kevin T Truong
*Assistant Examiner* — Samuel Hanna
(74) *Attorney, Agent, or Firm* — Palmer IP

(57) ABSTRACT

A supplementary blade for a speculum is disclosed, the speculum having a plurality of primary blades movable relative to each other for opening and closing, wherein the supplementary blade comprises an anchor portion attachable to the speculum and a blade portion movable with respect to the anchor portion, and the blade portion is shaped to interact with at least one of the primary blades to move into an extended position in response to opening of the primary blades.

A speculum is disclosed having a plurality of primary blades movable relative to each other for opening and closing, wherein at least one of the blades comprises a means for attaching a supplementary blade thereto to increase the functional length of the at least one blade.

16 Claims, 9 Drawing Sheets

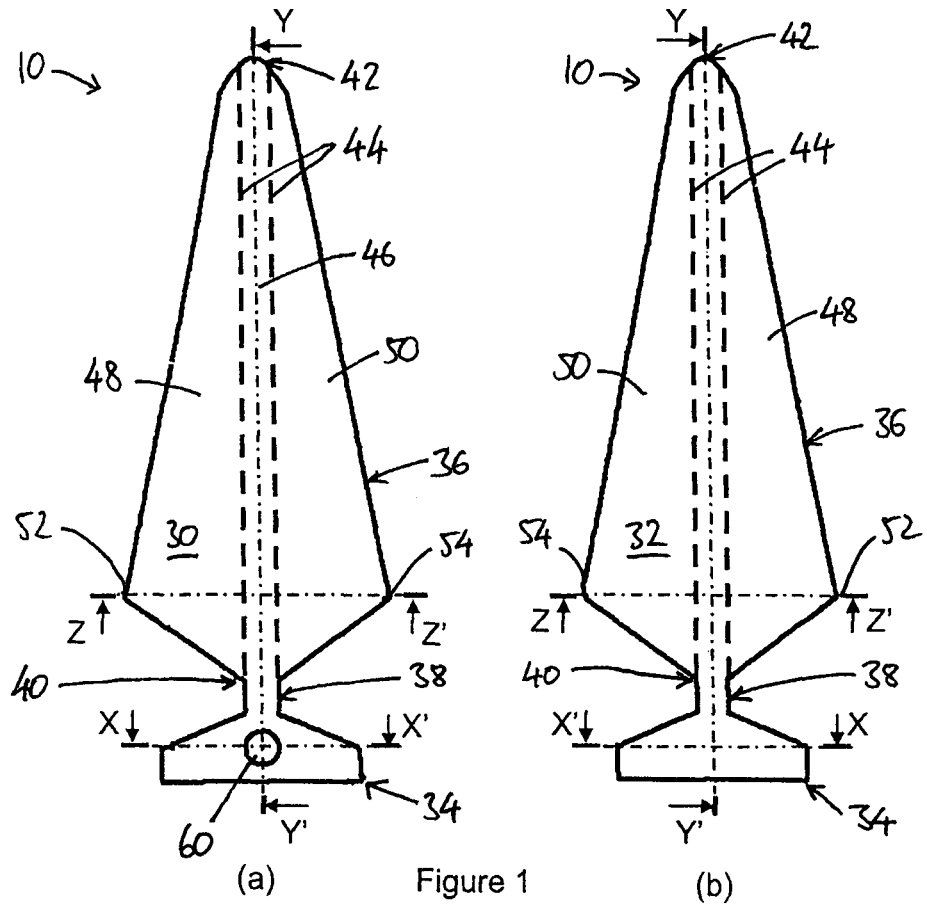
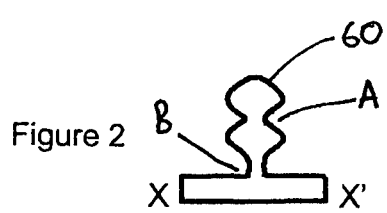
Figure 2
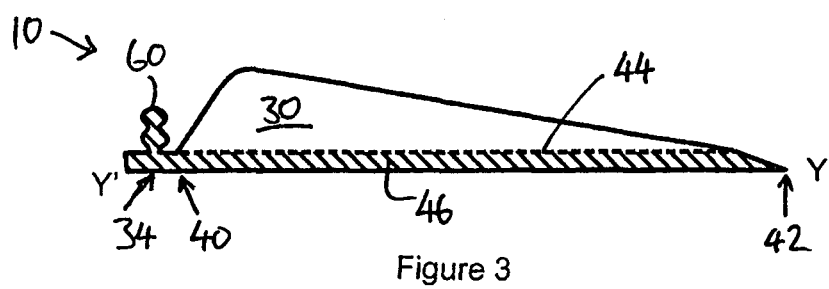
Figure 3

SPECULA

FIELD OF THE INVENTION

The present invention relates to a speculum, and in particular to a vaginal speculum for enabling examination and treatment of the vaginal walls and cervix.

BACKGROUND OF THE INVENTION

As is generally known, vaginal specula are used by physicians for dilating the opening of the vaginal cavity in order that the vaginal walls and cervix may be more easily visible and accessible for examination, diagnosis and treatment by surgery or otherwise.

Standard bivalve specula typically comprise two blades (an upper blade and a lower blade), joined near their proximal ends by a fixed hinge. At least one of the blades includes a handle, depending from the proximal end of the blade, for the physician to hold. The co-operating proximal end portions of the blades define a proximal aperture, through which aperture the physician may observe and access the vaginal cavity and cervix with instruments for inspection, investigation or surgery. Commonly the handle comprises two operating levers that can be moved relative to one another to open or close the blades.

In use, the speculum is positioned in the vaginal canal so that the upper blade is adjacent the top of the vaginal canal and the lower blade is adjacent the bottom of the vaginal canal. The blades are then splayed apart by operation of the levers to dilate the vaginal canal by pressing apart its top and bottom. In view of the fixed hinge, the dilation of the vaginal canal is greatest at the distal ends of the blades and decreases towards their proximal ends.

Typically, specula are also provided with a locking mechanism for locking the blades in position against vaginal wall muscle contraction once opened to a desired extent. A typical locking mechanism comprises a threaded rod joined by a pivot to one operating lever and a nut in threaded engagement with the rod and which can be tightened against the other operating lever. It will be appreciated that locking the position of the open blades requires both hands and can be an awkward manoeuvre.

Although the bivalve speculum is effective in widening the cervical end of the vaginal canal by splaying apart the blades, the access to the vaginal canal is determined by the diameter of the introitus of the vagina, and hence by the proximal aperture which normally cannot be widened any further. It will be appreciated that better access may be required during some treatments such as surgical procedures or in order to use certain medical instruments.

Accordingly, mobile-hinged specula, such as Graves' speculum, exist in which the upper and lower blades are not directly joined together so that the upper blade and the lower blade can be moved apart without the distal ends of the blades splaying apart. However, although this is a more adaptable speculum than the conventional fixed-hinge type, it is more complicated and more time-consuming to operate because the blade separation, blade flaring and locking operations all involve separate actions and are difficult or impossible to perform with one hand. This protracted routine is also not desirable from the point of view of the patient who would prefer the examination or treatment to be quick and to require generally less manipulation of the speculum.

A further problem associated with most speculum designs is that the handle or handles of the specula are normally at an acute angle, or at a right angle, to the blades. This inevitably results in the physician's hands and fingers being in contact with, or in close proximity to, the patient's genitalia, upper thighs and buttocks during a gynaecological procedure, which may be distressing to the patient and lead to accusations of impropriety against the physician.

Known speculum designs are ineffective in the case of patients having lax vaginal walls which prolapse and protrude inwardly between the open blades of the speculum in use, thus obstructing the physician's view and access and hindering procedures such as cervical smear-taking and treatment such as electrosurgery.

To overcome vaginal side wall prolapse, four-bladed specula are known in the art in which two additional blades are provided for supporting and pressing back the vaginal side walls during examination and treatment. Specula of this type are described in U.S. Pat. No. 5,868,668 and U.S. Pat. No. 6,024,696. In some cases, however, the additional blades must be manually operated by the physician when the speculum is in position, in addition to operation of the upper and lower blades as aforesaid. This inevitably requires the use and co-ordination of both hands which is cumbersome and awkward for the physician and also delays the procedure while both hands of the physician are occupied in operating the speculum. It is also unpleasant for the patient who may feel both of the physician's hands come into contact with, or be in proximity to, her genitalia, upper thighs and buttocks.

These problems have been partially overcome by the applicant's earlier invention as disclosed in WO 00/69325, which describes a speculum having two blades joined near their proximal ends by a floating hinge or pivot which allows the blades to move apart to widen the proximal opening without the blades necessarily splaying apart. Advantageously, the speculum includes an operating mechanism which allows one-handed operation. Also described are supplementary blades attached to the lower blade whose lateral splaying can also be controlled with one hand. Further, the operating lever and handle are obtusely angled in a proximal direction with reference to the blades so that the physician's hands and fingers are spaced further away from the patient's body when operating the speculum.

Although the floating hinge allows some widening of the proximal opening and therefore access into the vaginal cavity, this widening is limited by the length of the floating hinge itself and so this speculum is still not appropriate for use with some surgical procedures where a yet wider access is required into the vaginal cavity.

Additionally, the supplementary blades and associated parts make it difficult to clean and sterilise the instrument. This is especially pertinent in light of the current fear of MRSA 'super-bug' infections in hospitals and clinics. To combat the spread of MRSA, it is now policy in most if not all hospitals to dispose of medical instruments after single use unless their construction allows for effective cleaning and sterilisation. Undoubtedly, this would mean that the speculum described in WO 00/69325, as well as other similar prior art instruments such as those disclosed in U.S. Pat. No. 6,048,308 and WO 99/12466, would be treated as single-use instruments because of their construction and so disposed of after one use. However, the cost of manufacture of these complex instruments can be high. In addition, the design of such specula can necessitate the use of metals, with the associated fabrication and material costs being higher than if plastics could be used. It is apparent that the resulting wastage, both in terms of costs and materials, is significant. If instruments are to be disposable, one use only, they need to be as simple and inexpensive as possible but without losing functionality.

BRIEF SUMMARY OF THE INVENTION

The invention aims to provide a vaginal speculum which overcomes or minimises the problems mentioned above.

From one aspect, the invention resides in a supplementary blade for a speculum, the speculum having a plurality of primary blades movable relative to each other for opening and closing, wherein the supplementary blade comprises an anchor portion attachable to the speculum and a blade portion movable with respect to the anchor portion, and the blade portion is shaped to interact with at least one of the primary blades to move into an extended position in response to opening of the primary blades. Preferably, the supplementary blade is resilient to return to a retracted position when the primary blades close. The supplementary blade has a concave inner face shaped to lie against a convex outer surface of one or more of the primary blades, and may for example have at least one wing lying outside a plane containing the anchor portion.

Advantageously, lax vaginal side walls can be pushed back or supported by the supplementary blade in the extended position. This is in addition to the effect of the open primary blades of the speculum on the vaginal walls, and allows a practitioner to carry out observation or treatment of the vagina or cervix without hindrance. As the movement of the supplementary blade between the extended and the retracted positions results from the interaction between the blade portion of the supplementary blade and at least one of the primary blades, no additional levers or handles are required for its operation. This means that a physician can operate the speculum with one hand and use the other hand for taking samples and/or treatment if required, which causes less discomfort to the patient and a faster overall procedure than using a more complex speculum.

Preferably, the supplementary blade has a discontinuous lateral cross-section interrupted by two parallel creases and the cross-section includes two or more generally flat portions extending from each crease. The supplementary blade preferably also has a major portion tapering generally toward a free end opposed to the anchor portion, a minor portion tapering generally toward the anchor portion and a neck joining the anchor portion to the blade portion. The lateral cross-section of the supplementary blade comprises a spine and two wings lying to the same side of the spine and is symmetrical about the central longitudinal axis of the spine.

Conveniently, the supplementary blade is attachable to a speculum by means of a releasable fastening on the anchor portion, the releasable fastening preferably comprising a stud engageable within a hole in the speculum. This means that the supplementary blade need only be attached to the speculum when required or detached in circumstances when it is not required. Additionally, the releasable fastening on the anchor portion is such that the supplementary blade can be used with existing and conventional specula designs and so there is no need to adapt existing equipment. As the supplementary blades have such a simple construction and can be easily made from plastics, they are cheap to manufacture. The supplementary blades, or specula fitted with the supplementary blades, are therefore viable as disposable devices. Alternatively, the supplementary blades can be cleaned and sterilised separately from the speculum.

A further advantage of the supplementary blade is that its anchor portion comprises a fastening attachable to a speculum in two or more attachment positions, a first attachment position being laterally inward of a second attachment position. The stud has two or more waists each defining a respective attachment position. These two or more attachment positions means that the desired extension of the supplementary blade in the extended position can be controlled or chosen according to the patient and the situation.

The invention also extends to a speculum having a plurality of primary blades movable relative to each other for opening and closing, and being fitted with at least one supplementary blade, the supplementary blade being positioned to interact with at least one of the primary blades to move into an extended position in response to opening of the primary blades.

The invention also includes a speculum having a plurality of primary blades movable relative to each other for opening and closing, wherein at least one of the blades comprises a means for attaching a supplementary blade thereto to increase the functional length of the at least one blade. Advantageously, the attachment means comprises an opening for receiving a portion of the supplementary blade to attach it to the at least one blade. In a preferred embodiment, the opening comprises a channel for receiving a portion of the supplementary blade, the supplementary blade being movable within said channel to vary the functional length of the blade.

The present invention extends to a speculum comprising first and second blades whose opening and closing is controlled by manipulating respective handles, wherein at least one of the handles comprises ratchet means engageable by the other of said handles.

Advantageously, the ratchet means is on a platform extending rearwardly from one of the handles and the other of the handles moves across the platform when the handles are manipulated in use. The platform may carry a series of protrusions, for example transverse ridges. Advantageously, the other of the handles has a free edge co-operable with the protrusions and, optionally, comprises two or more engagement means for engagement with the ratchet means.

Preferably, if two or more engagement means are provided, they are spaced along the handle and are selectable by moving the handles about a floating hinge to bring the ratchet means into co-operation with the selected one of the engagement means. Such an engagement means may be defined by an edge of an opening in a handle.

By virtue of these features, the speculum can be locked in the open blade position more easily than with the typical nut/screw locking mechanism of conventional specula. The physician can lock the blades of the speculum into position using only one hand which is more comfortable for the patient and speeds up the procedure.

A thumb rest may protrude from a free end of at least one of the handles. This assists the physician in operating the handles of the speculum and in locking the blades in position.

The present invention also includes a package comprising a wrapper encapsulating at least part of a medical instrument such as a speculum, the package containing lubricant between the wrapper and the instrument to lubricate at least an encapsulated part of the instrument before removal of the wrapper.

Advantageously, the incorporation of the lubricant facilitates the use of the medical instrument such as the insertion of the speculum into a cavity of the patient.

Advantageously, at least the encapsulated part of the instrument is pre-lubricated with lubricant before being encapsulated in the wrapper. This means that the pre-lubricated and encapsulated instrument can be a sterile unit, which is ready for the practitioner to use. Advantageously, the practitioner need not spend time smearing lubricant over the instrument with his fingers before use which might increase the chances of contamination.

Preferably, lubricant is localised within the wrapper, and is optionally confined to its location within the wrapper. In a preferred embodiment, the lubricant is confined by a breachable barrier within the wrapper. The material of the barrier is suitably weaker than the material of the wrapper, such that, for example, the barrier can be breached by user pressure upon the exterior of the wrapper. Alternatively, the barrier can be breached under pressure from the instrument, or by a combination of user and instrument pressure.

Advantageously, lubricant is localised adjacent a distal end of the instrument within the wrapper. However, the wrapper is preferably flexible such that lubricant can be distributed over the instrument upon manipulation of the wrapper.

The wrapper preferably completely encapsulates the instrument but the wrapper may comprise a minor compartment containing lubricant and a major compartment for encapsulating at least part of the instrument.

The invention further includes a method of lubricating a medical instrument before use, comprising supplying the instrument at least partially encapsulated in a wrapper with lubricant between the wrapper and the instrument, and manipulating the wrapper to distribute lubricant over the instrument before removal of the wrapper. The lubricant is preferably initially localised within the wrapper and is preferably confined by a breachable barrier within the wrapper. In this case, the method suitably comprises manipulating the wrapper and/or the instrument to breach the barrier for distribution of the lubricant over the instrument.

BRIEF DESCRIPTION OF THE SEVERAL VIEWS OF THE DRAWINGS

In order that this invention may be more readily understood, currently preferred embodiments will now be further described by way of example with reference to the accompanying drawings, in which:

FIG. 1 is a plan view of (a) an inside face, and (b) an outside face of a supplementary blade according to the present invention;

FIG. 2 is a cross-sectional view on line X-X' of the supplementary blade of FIG. 1 when viewed from the proximal end;

FIG. 3 is a cross-sectional view on line Y-Y' of the supplementary blade of FIG. 1;

DETAILED DESCRIPTION OF THE INVENTION

Figure 4:
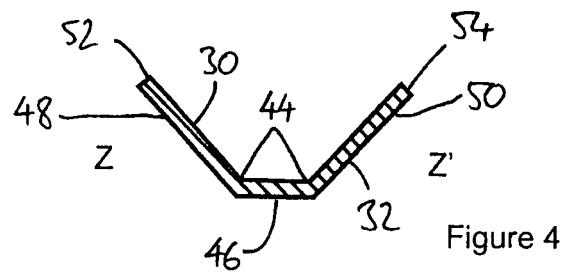
FIG. 4 is a cross-sectional view on line Z-Z' of the supplementary blade of FIG. 1.

Referring initially to FIGS. 1 to 4, there is shown a supplementary blade 10 which can be attached or fixed to a conventional speculum 12 (shown in part in FIGS. 5 to 8) the conventional speculum 12 typically having two primary blades, an upper blade 14 and a lower blade 16, which are joined or co-operate near their proximal ends 17 by a hinge, pivot or fulcrum. Typically, the hinge 18 comprises two co-axial joints 20.

The co-operating proximal end portions 17 of the primary blades 14, 16 define a proximal aperture (not shown) through which the vaginal cavity of a patient can be accessed. In conventional manner, the primary blades 14, 16 and the hinge 18 are arranged so that the blades 14, 16 can be moved apart, about the joints 20, to splay apart the blades 14, 16 which pushes back the vaginal walls of a patient in use. Although not shown in these figures, the supplementary blade 10 of the present invention may also be used with a speculum in which the proximal ends of the primary blades are able to move apart to widen the proximal opening.

The supplementary blade 10 is intended to push back or support vaginal side walls in patients with lax vaginal walls, in other situations where there is a risk of prolapse of the vaginal walls, or where prolapse has occurred. The supplementary blade 10 has an inside face 30 and an outside face 32 and comprises an anchor portion 34, a blade portion 36 and a hinge portion 38. The length of the blade portion 36 is approximately three quarters of the length of a primary blade of a conventional speculum.

Figure 9:
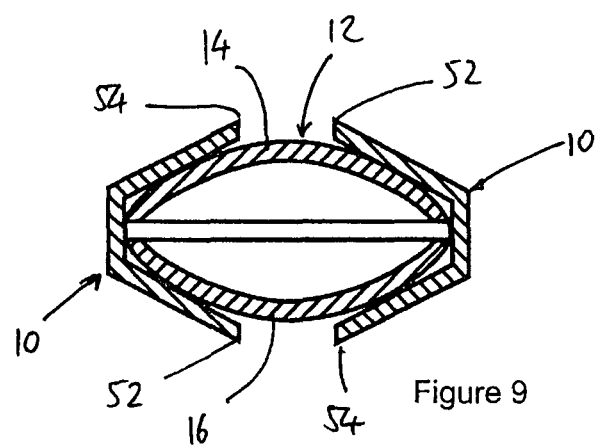
FIG. 9 is a cross-sectional view through the line Z-Z' of the supplementary blade of FIG. 1 when attached to the conventional speculum of FIG. 5, when the primary blades of the speculum are in the closed position.
Figure 10:
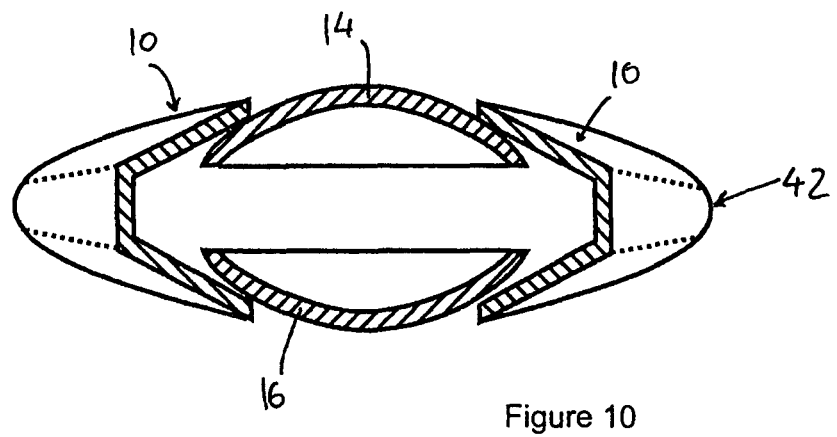
FIG. 10 is a cross-sectional view through the line Z-Z' of the supplementary blade of FIG. 1 when attached to the conventional speculum of FIG. 5, when the primary blades of the speculum are in the open position.

The blade portion 36 is generally trowel-shaped in that moving from its proximal end 40, it widens to a maximum width near its proximal end 40 and then tapers along its length towards its distal end 42. Further, the blade portion 36 has a concave inside face 30 whose shape complements the convex outside curvature of the two primary blades 14, 16 of a conventional speculum 12 when the primary blades 14, 16 are in a closed position. Creases 44 run along the length of the blade portion which subdivide the blade portion 36 into a planar spine section 46 and two wing sections 48, 50, each wing section 48, 50 having wing tips 52, 54 corresponding to the maximum width of the blade portion 36. The anchor portion 34 and the spine section 46 of the blade portion 36 lie on substantially the same plane when the supplementary blade 10 is at rest. In this embodiment, the two wing sections 48, 50 are folded about the creases 44 such that the wing tips 52, 54 lie in a common plane parallel to that of the spine section 46, as will be seen clearly from FIGS. 4, 9 and 10. Alternatively, the blade portion 36 may have only one crease running 44 along its length such that the blade portion 36 is 'V' shaped in cross-section, or equally the blade portion 36 may have no creases and be 'U' shaped in cross-section. The conceptual link here is that the blade portion 36 has at least one wing tip which lies on a different plane from that of the spine section 46 or the anchor portion 34 of the supplemental blade 10.

The blade portion 36 is made of a material, for example a stiff polymer, which is rigid enough to maintain its general shape and contour during use; however, the material may advantageously offer some flexibility and resilience. The hinge portion 38 joins the blade portion 36 to the anchor portion 34 and can be integral with both the blade 36 and anchor portions 34, or separate from them but joined to them. Whilst the anchor portion 34 is attached to the speculum 12 and relatively immobile in relation to the speculum 12, the hinge portion 38 allows the lateral movement of the supplementary blade portion 36 in use. If the supplementary blade 10 is a single piece construction, such as a moulded plastic item, this flexibility at the hinge portion 34 may be achieved by having a reduced thickness at the hinge portion 34, or alternatively forming the hinge portion 34 so that it is adapted to flex, such as a crease or score or a concertina formation. If, alternatively, the supplementary blade 10 is not formed as one-piece, the blade portion 36 and the anchor portion 34 may be formed separately and be joined together such that the join between them forms the hinge portion 34.

The anchor portion 34 comprises an attachment means, such as a fastener 60, for attaching the supplementary blade 10 to the speculum 12. Preferably, the fastener 60 is a pin, stud or toggle which is resiliently press-fitted into the existing joint 20 of the speculum 12 without requiring adaptation of the speculum 12. It will be noted in this respect that the joint 20 of a speculum is commonly a hollow rivet defining a hole that can receive the fastener 60 of the supplementary blade 10. However, alternative fixings such as adhesives will be apparent to the reader. It is also preferred that fixings are releasable so that if the physician decides not to use the supplementary blades for any reason, they can be removed and discarded.

In use, the supplementary blade 10 is positioned on and attached to a joint 20 of the speculum hinge 18 by its fastener 60 so that the inside face 30 of the supplementary blade 10 faces and embraces the outside faces of the primary blades 14, 16 of the speculum. It is envisaged that two supplementary blades 10 of the present invention will be used with a speculum 12, each blade 10 being attached to one of the two hinge joints 20, on either side of the speculum 12.

When the primary blades 14, 16 of the speculum 12 are in the closed position, the supplementary blades 10 lie close enough to the primary blades 14, 16 that the speculum 12 with its supplementary blades 10 can be inserted smoothly into the vaginal cavity. It will be noted in particular that the distal region 42 of each supplementary blade 10 is in contact with, or lies close to, the primary blades 14, 16 when the primary blades 14, 16 are in the closed position.

As can be seen most clearly from FIG. 2, the fastener 60 has a double-waisted cross-section shape to provide two positions of attachment of the supplementary blade 10 relative to the speculum 12, marked A and B. It will be appreciated that when the supplementary blade 10 is attached to the speculum 12 in the first position A, the anchor portion 34 and hence the proximal end 40 of the blade portion 36 of the supplementary blade 10 is spaced further apart from the primary blades 14, 16 of the speculum 12 than when the attachment is in the second position B. The two attachment positions A, B provide a different supplemental blade splaying effect, which will be described below with reference to FIGS. 5 to 10.

Referring now to FIGS. 5 to 10, in use, as the primary blades 14, 16 of the speculum 12 are opened or splayed in conventional manner, the supplementary blade 10 attached to the speculum 12 is caused to splay outwards away from the body of the speculum 12 through interaction with at least one (and in this embodiment, both) of the primary blades 14, 16. When inside the vaginal cavity, the outward splaying of the supplementary blade 10 pushes back the vaginal side walls affording the physician unhindered access to the vaginal canal for examination or treatment. Initially, when the primary blades 14, 16 are closed, at least the distal region 42 of the blade portion 36 of the supplementary blade 10 is in contact with at least one primary blade. As the primary blades 14, 16 are opened further apart and the supplementary blade 10 splays further outward, the leading area of contact on the blade portion 36 moves proximally, until it reaches or approaches the wing tip 52, 54, at which point the supplementary blade portion 10 is at its maximum splay position. This can be most clearly seen in FIG. 10.

When the supplementary blade 10 is attached to the speculum 12 at position A of the fastener 60, the proximal end 40 of the supplementary blade 10 with the associated wing tips 52, 54 is spaced further away from the primary blades 14, 16 of the speculum 12.

This means that the supplementary blade 10 is caused to splay away from the body of the speculum 12 later in the opening movement, i.e. when the primary blades 14, 16 are open further, compared with attachment position B. In other words, attachment position A is chosen when a milder lateral splay effect is required.

Although not shown, the present invention also includes a further embodiment of the supplementary blade 10 of FIG. 1 wherein the anchor portion 34, the blade portion 36 and the hinge portion 38 are substantially immobile in relation to each other.

Figure 11:
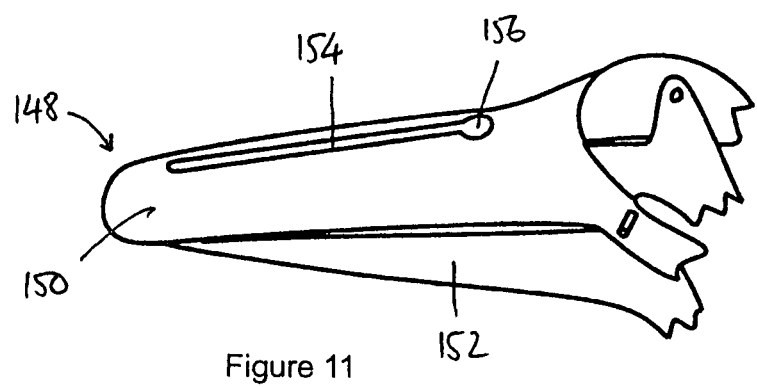
FIG. 11 is a perspective view of a modified speculum according to the present invention.

FIG. 11 shows an alternative speculum 148 which differs from the conventional speculum 12 of FIGS. 5 to 10 in that it includes an upper blade 150 and a lower blade 152, each of which include a substantially rectangular slot, channel or guiding means 154 extending between the distal and proximal ends of the blades 150, 152. Each slot 154 is centrally positioned with respect to its associated blade 150, 152 and terminates at its proximal end with an opening 156 slightly wider than the width of the slot 154.

Figure 12:
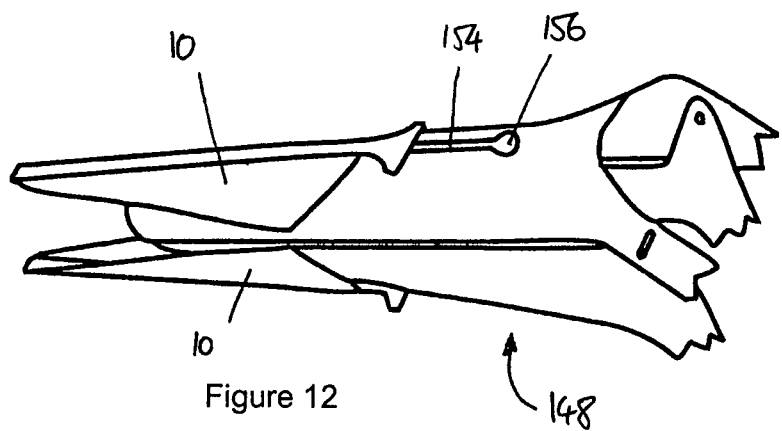
FIG. 12 is a perspective view of the speculum of FIG. 11 assembled with the supplementary blade of FIG. 1.

As can most clearly be seen in FIG. 12, the speculum 148 is intended to be assembled with a supplementary blade, such as the supplementary blade 10 of FIG. 1, to increase the functional length of the speculum 148. The proximal opening 156 of the slot 154 is shaped to receive the fastener 60 of the supplementary blade 10 by press-fitting. Once assembled, the supplementary blade 10 can be slid along the length of the slot 154 to vary the functional length of the speculum 148.

Although FIGS. 11 and 12 show the speculum 148 including a slot 154 on both its upper and lower blades 150, 152, it is also possible to provide a slot 154 on only one of the blades 150, 152 so that the length of the speculum 148 is variable on only one side. Similarly, where slots 154 are provided on both of the upper and lower blades 150, 152, their supplementary blades 10 can be extended to different functional lengths.

In another arrangement, not shown, it is possible to replace the slots 154 with a linear array of holes spaced along the length of the upper and/or lower blades 150, 152. This provides a plurality of selectable anchorage points to choose for various functional lengths.

The present invention also contemplates a conventional speculum 12 adapted to include one or more of the slots 154 described above on its upper and/or lower blades 14, 16.

Referring now to FIGS. 13 to 16, the invention also contemplates a speculum 80 having a simplified locking mechanism for locking the position of the open blades. The speculum 80 comprises an upper blade 82 and a lower blade 84 of substantially conventional shape, the upper and lower blades 82, 84 having associated upper and lower handles 86, 88, respectively. The upper and lower blades 82, 84 are connectable to each other at their proximal ends by a hinge 89, the hinge 89 comprising two joints 91, one on each side of the blades 82, 84. Each joint 91 consists of a pin 90 formed at, or joined to, the proximal end of the lower blade 84 (as can most clearly be seen in FIG. 14) and an opening 92 for receiving the pin 90, at the proximal end of the upper blade 82. Alternatively, the pin 90 may be formed at, or joined to the upper blade 82, and the opening on the lower blade 84. As before, the proximal ends of the upper and lower blades 82, 84 define a proximal aperture, through which the vaginal canal can be accessed in use.

Both the upper and lower handles 86, 88 depend from the proximal ends of the upper and lower blades 82, 84, respectively, at an obtuse angle to the blades 82, 84. In other words, the upper and lower handles 86, 88 depend rearwardly or proximally from the blades 82, 84. The angle of the upper handle 86 from the upper blade 82 is less than the angle of the lower handle 88 from the lower blade 84. Squeezing the handles 86, 88 together, or pressing the upper handle 86 distally towards the lower handle 88 flares the blades 82, 84 apart at their distal ends. In conventional manner, the separation of the blades 82, 84 is greatest at their distal ends and decreases towards their proximal ends.

Conveniently, in use, the position of the flared blades 82, 84 can be held or locked in position against inward pressure from the vaginal walls by a ratchet means 96 which comprises a ratchet portion 98 on the lower handle 88, and an edge 100 at the free end 101 of the upper handle 86 co-operable with the ratchet portion 98. The ratchet portion 98 comprises a series of protrusions 102 or teeth and is at the free end 104 of the lower handle, depending orthogonally rearwardly from the handle 88. An open blade position is held or locked by engaging or abutting the edge 100 at the free end of the upper handle 86 against one of the protrusions 102, by virtue of the open blades 82, 84 being in compression from contraction of the vaginal wall muscles.

The upper and lower blades 82, 84 can be easily disconnected from each other by virtue of the pin and hole arrangement of the joint 91 and some flexibility of the material from which the blades are made. This provides the physician with greater flexibility during examination and treatment, such as when better access is required through the introitus of the vagina to accommodate certain medical instruments. In this case the lower blade 84 and upper blade 82 are detached or disassembled from each other and either one or both of the blades are used as a retractor or retractors.

Figure 13:
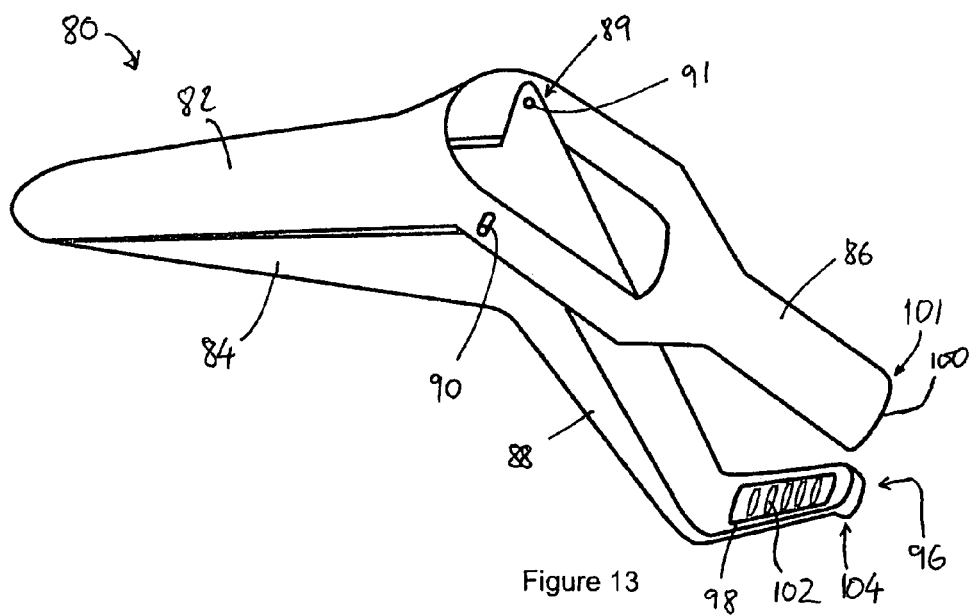
FIG. 13 is a perspective view of a speculum of the present invention, having an upper blade and handle and a lower blade and handle.
Figure 14:
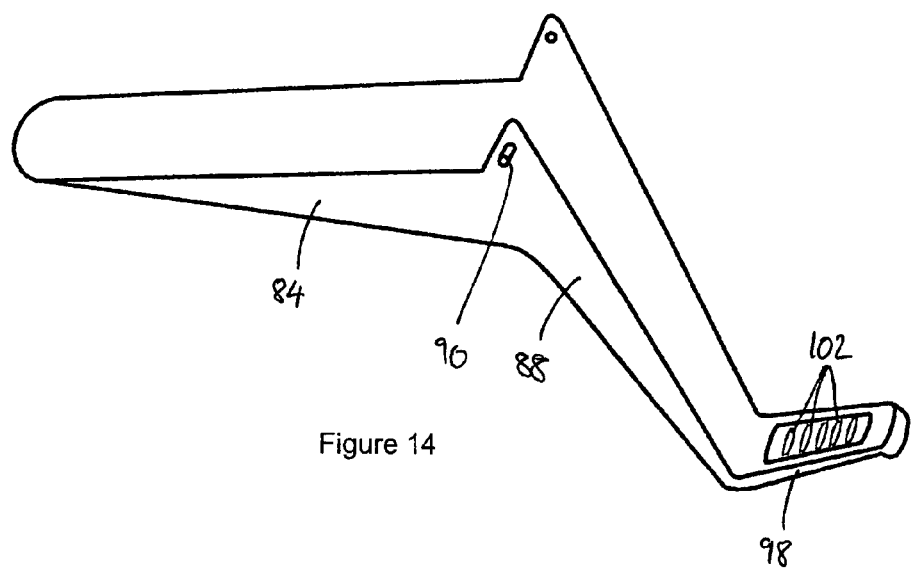
FIG. 14 is a perspective view of the lower blade and handle of the speculum of FIG. 13.
Figure 15:
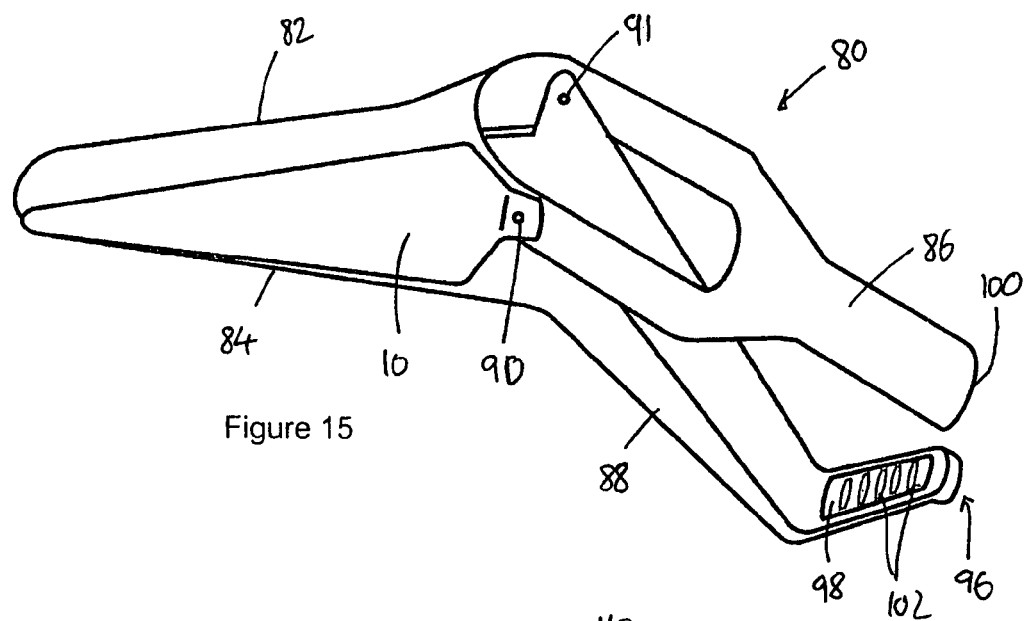
FIG. 15 is a perspective view of the speculum of FIG. 13 assembled with the supplemental blade of FIG. 1.

FIG. 15 shows the speculum 80 of FIG. 13 assembled with the supplementary blade 10 featured in FIGS. 1 to 10. Operation of this speculum 80 results in lateral splaying of the supplementary blade 10 through co-operation with at least one of the speculum blades, as described above with reference to FIGS. 1 to 10.

Figure 16:
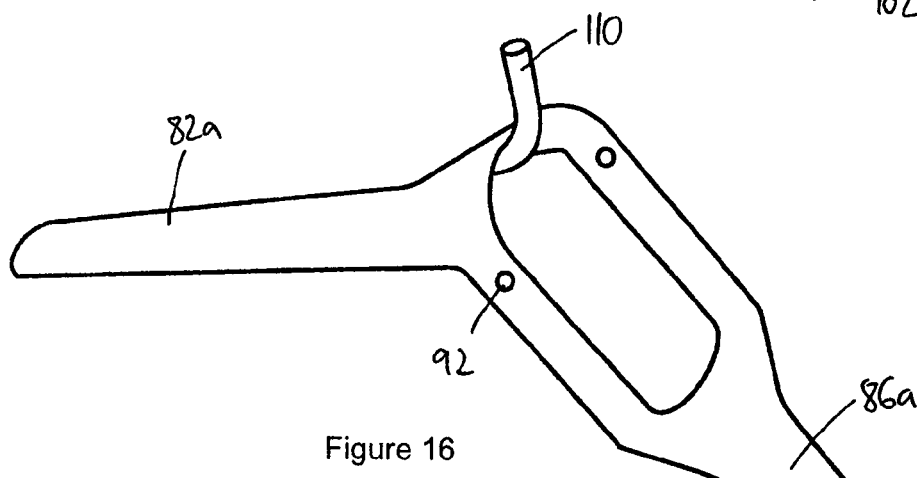
FIG. 16 is a perspective view from the side of a variant of the upper blade and handle of the speculum of FIG. 13.

FIG. 16 shows an alternative upper blade 82*a* and handle 86*a* construction to that shown in FIGS. 13 and 15, having a smoke extraction tube 110 incorporated into the proximal end of the upper blade 82*a*.

Figure 17:
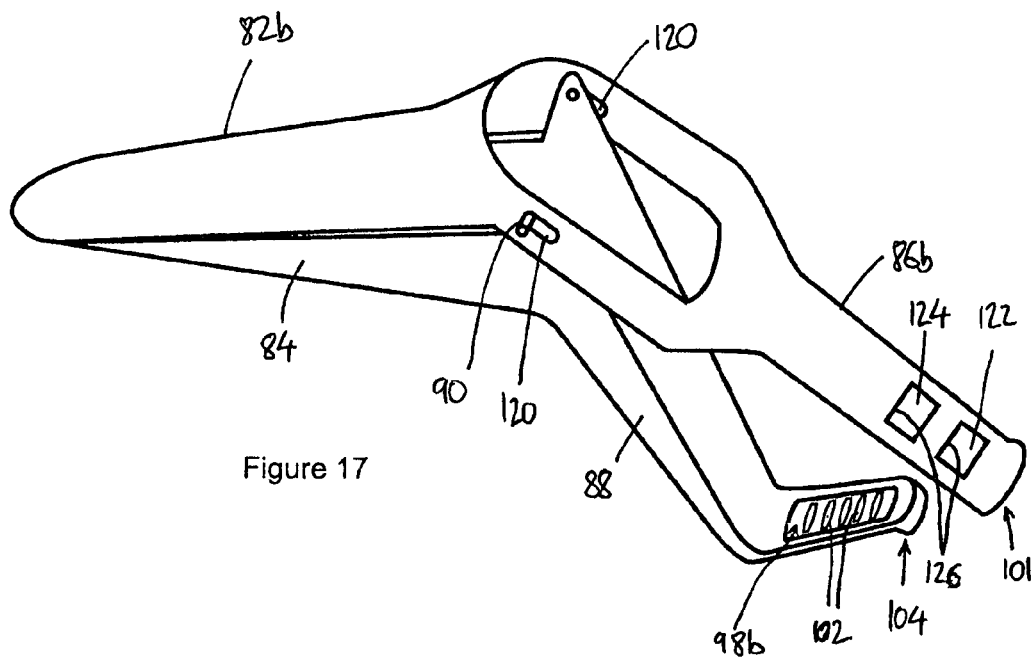
FIG. 17 is a perspective view from the side of an alternative embodiment of the speculum of FIG. 13.
Figure 18:
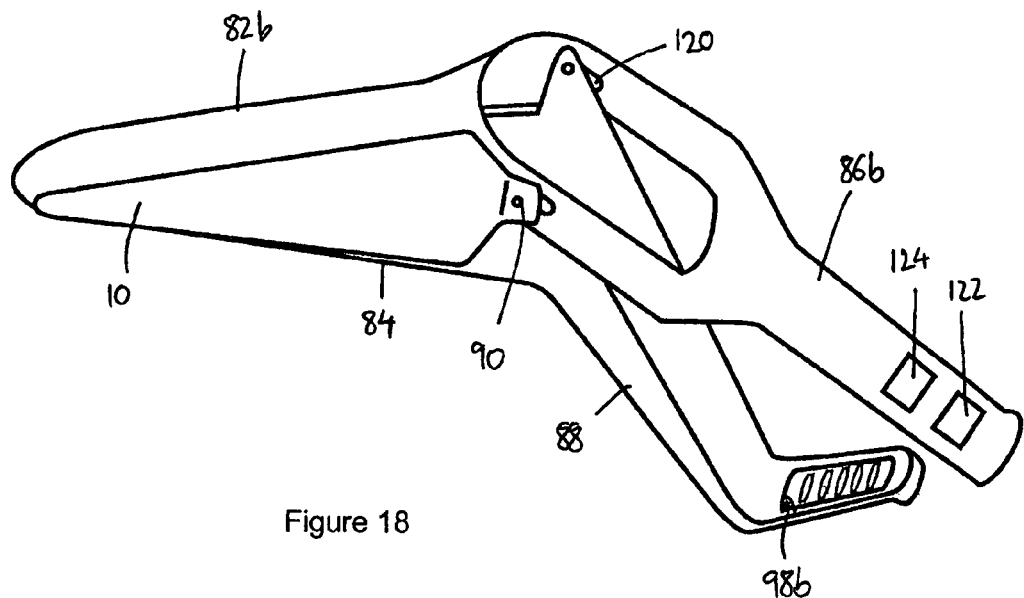
FIG. 18 is a perspective view from the side of the speculum of FIG. 17 assembled with the supplemental blade of FIG. 1.
Figure 19:
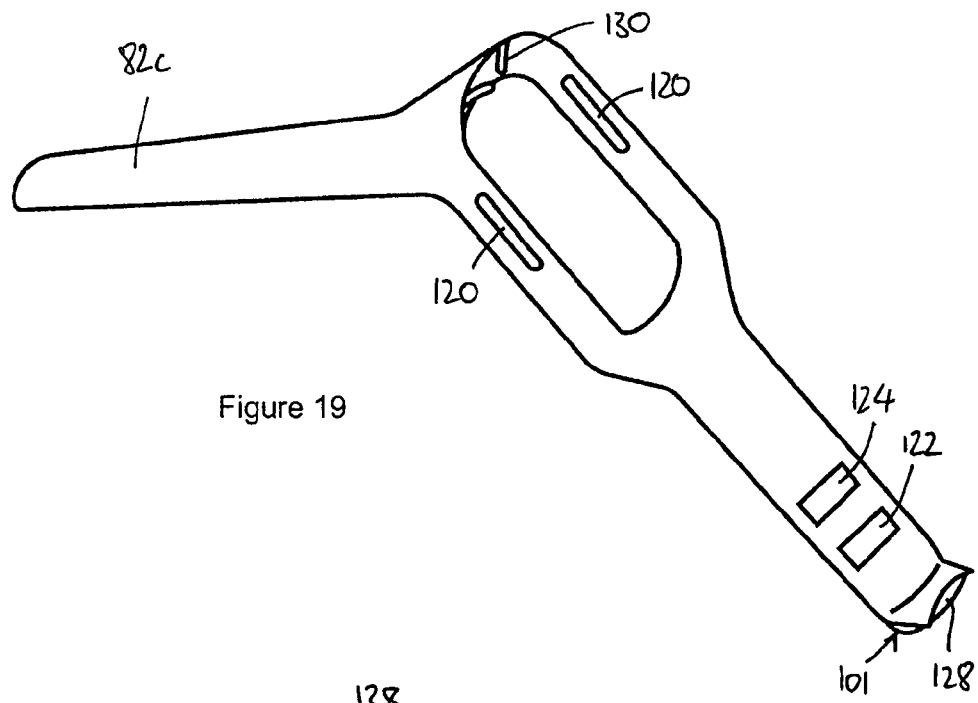
FIG. 19 is a perspective view from the side of a variant of the upper blade and handle of the speculum of FIG. 17.

FIGS. 17 to 19 show alternative embodiments of the specula of FIGS. 13 to 16, having a further alternative upper blade 82*b* and handle 86*b* construction, which allows increased dilation of the introitus of the vagina without disassembling. The hinge between the upper blade 82*b* and the lower blade 84 is a mobile or floating hinge 89*b*, defined by each joint 91*b* comprising an elongated opening or slot 120 on the upper blade 82*b* for receiving the pin 90 of the lower blade 84. It will be appreciated that the proximal opening is enlarged by moving the lower blade 84 and upper blade 82*b* relative to each other so that the pin 90 lies towards the handle end of the slot 120. The ratchet means of this alternative embodiment comprises a ratchet portion 98*b* at the free end 104 of the lower handle, as before, and two openings 122, 124 in the free end of the upper handle 86*b* which are wide enough to receive the ratchet portion 98*b*. In use, the flared apart position of the blades can be held or locked in place by the engagement of a protrusion 102 of the ratchet means 96*b* with an edge 126 of one of the openings 124. The lower opening 122 is selected when an enlarged proximal opening is required; conversely the upper opening 124 is selected when a smaller proximal opening is required. The upper and lower blades may also be detached or disassembled from each other, enabling one or both of the blades to be used as a retractor or retractors, and for ease of cleaning.

FIG. 18 shows the speculum of FIG. 17 assembled with the supplementary blade of FIGS. 1 to 10.

A variant of the upper blade of this alternative embodiment is shown in FIG. 19, having a thumb support 128 at the free end 101 of the upper handle, and clips 130 at the proximal end of the upper blade 82*c* for holding a smoke extraction tube which may be inserted into the vaginal cavity during electrosurgery, for example. The clips 130 may be separate parts attached to the upper blade 82*c* of the speculum but are preferably integral with the upper blade 82*c*, being tabs cut out and bent away from that blade. The construction of the speculum and thumb support 128 helps a physician to adjust the openings of the blades and lock them in position relative to each other using one hand.

Figure 5:
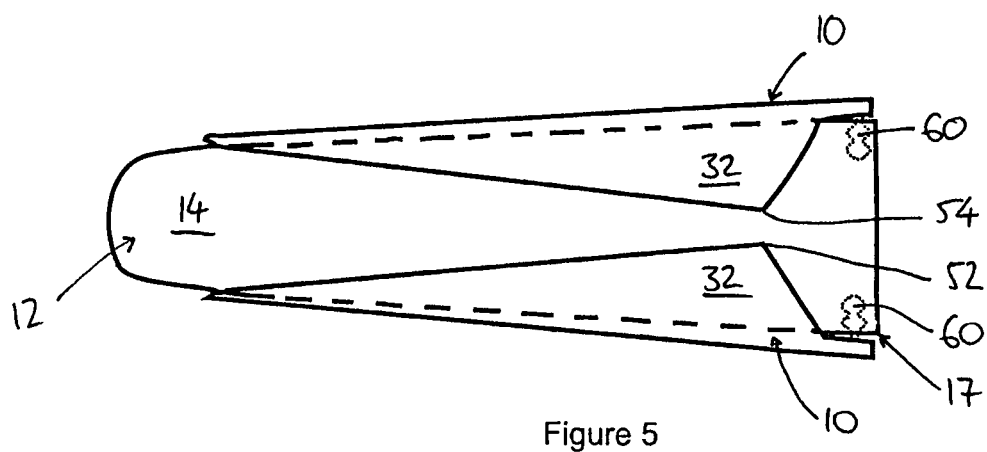
FIG. 5 is a top plan view of two supplementary blades of FIG. 1 attached to a conventional speculum having an upper and a lower primary blade, when the primary blades of the speculum are in a closed position.
Figure 6:
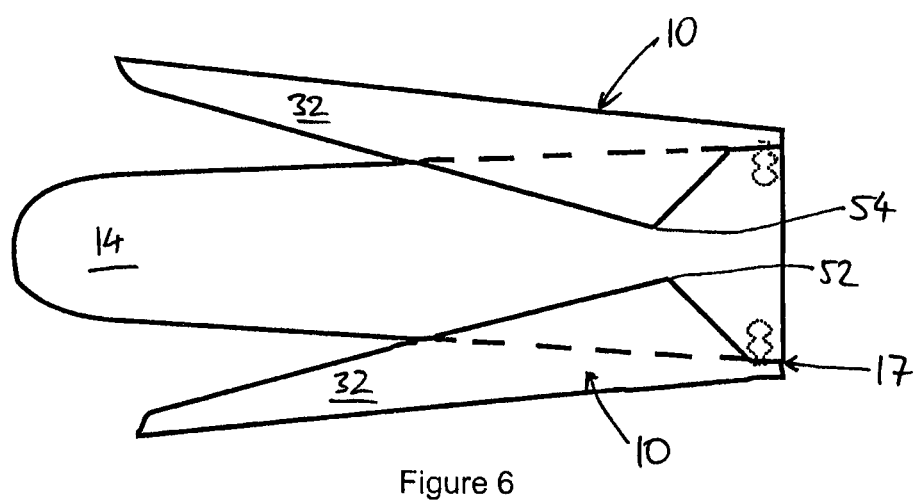
FIG. 6 is a top plan view corresponding to FIG. 5 but showing the splayed apart supplementary blades, when the primary blades of the speculum are in an open position.
Figure 7:
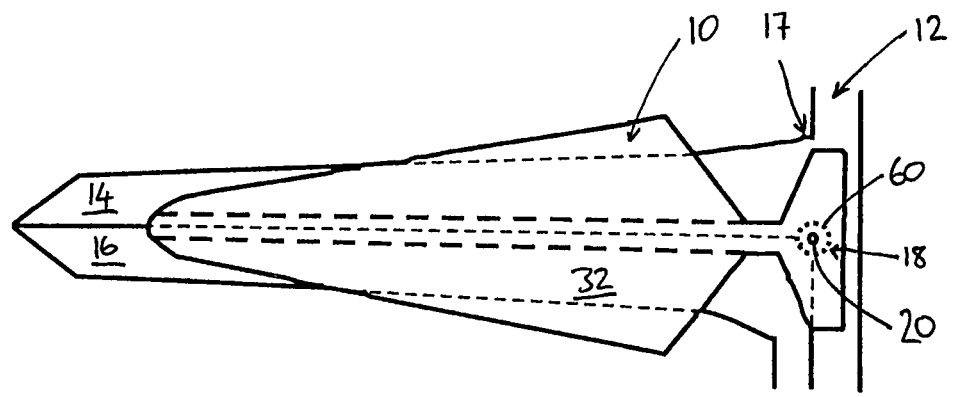
FIG. 7 is a side view of the supplementary blades and speculum arrangement of FIG. 5, when the primary blades of the speculum are in the closed position.
Figure 8:
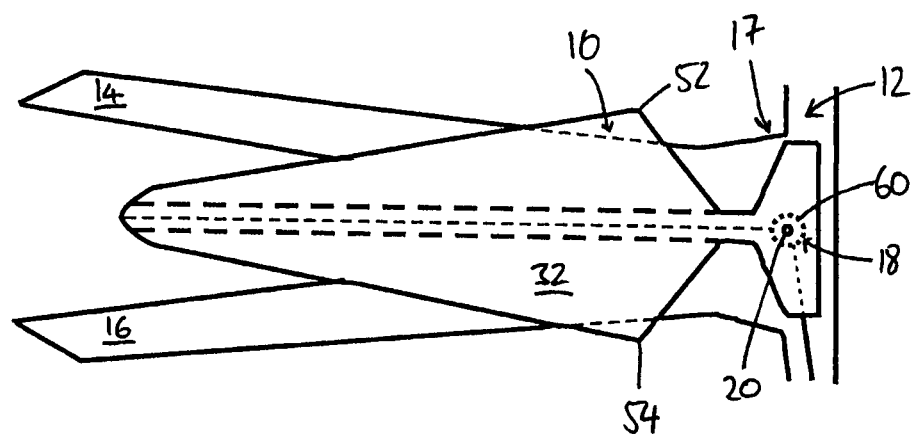
FIG. 8 is a side view of the supplementary blades and speculum arrangement of FIG. 6, when the primary blades of the speculum are in the open position.
Figure 20:
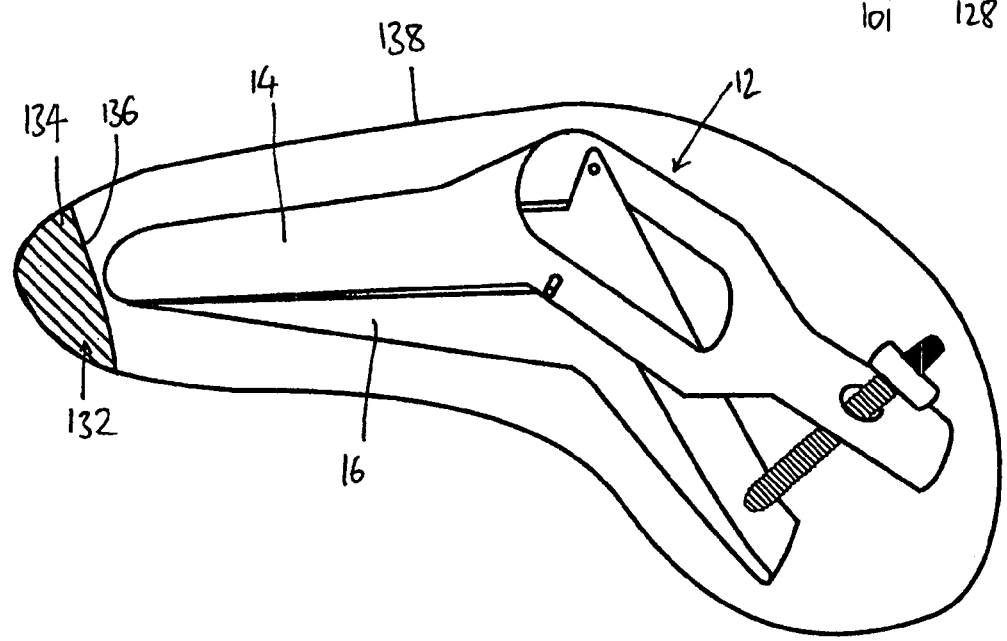
FIG. 20 is a perspective view of a conventional speculum having a lubrication packet of the present invention.

In FIG. 20 is shown the conventional speculum 12 of FIGS. 5 and 8 with two primary blades 14, 16 and having a lubrication means for lubricating the blades 14, 16 of the conventional speculum 12 for ease of insertion of the blades 14, 16 into the vaginal cavity of a patient. The lubrication means comprises a blister 132 containing a lubricant 134, such as KY Jelly (trade mark) or any other suitable lubricant, constrained by a thin membrane 136. The blister 132 is on the inside of a package 138 containing the sterile conventional speculum 12.

In use, a practitioner bursts the blister 132 of lubricant 134 to smear the lubricant 134 on the tips of the blades 14, 16 of the conventional speculum 12 by applying pressure on the membrane 136 with the blade tips, before opening the package 138. In this way, the practitioner avoids having to use his or her fingers to smear lubricant on the conventional speculum 12, and the conventional speculum 12 is lubricated while still within its sterile packaging. Although not shown, the lubrication means of the present invention can also be used with any of the specula of FIGS. 7 to 19. Also, the blister 132 may contain medicinal or therapeutic products such as antibiotic creams or lotions instead of, or as well as, the lubricant 134.

The present invention also contemplates an alternative lubrication means for specula, which comprises a pre-lubricated speculum sealed within the package 138. As before, a medicinal or therapeutic product may also or alternatively be applied to the speculum thus packaged.

The present invention may be embodied in other specific forms without departing from its essential attributes as defined in the appended claims and other statements of invention herein. For example, the invention in its broadest sense is not limited solely to gynaecological specula. Also, the shape, size and material of the speculum can be selected to suit particular circumstances.

The invention claimed is:

1. A speculum for opening a vaginal cavity comprising:
a plurality of primary blades extending along a longitudinal axis from a proximal end to a distal end, each primary blade comprising a convex outer surface, wherein the primary blades define at least upper and lower blades that are pivotally attached and movable relative to each other between opened and closed positions for opening and closing in a first direction, and
at least one supplementary blade extending along a longitudinal axis from a proximal end to a distal end, said at least one supplementary blade is fastened to a side of the speculum and configured to lie against a side wall of a vaginal cavity when in use, said at least one supplementary blade comprising:
a concave inner surface situated between the proximal and distal ends of the at least one supplementary blade,
an anchor portion at said proximal end of the at least one supplementary blade comprising a fastener, for fastening the at least one supplementary blade to the side of the speculum and
a blade portion comprising a contact area disposed on the concave inner surface, wherein the blade portion is movable with respect to the anchor portion and the blade portion is shaped to interact with at least one of the primary blades to move into an extended position through interaction with the convex outer surface of at least one of the primary blades; and
a hinge portion that joins the blade portion to the anchor portion to allow lateral movement of the blade portion relative to the anchor portions,
wherein the concave inner surface is shaped to lie against the convex outer surface of one or more of the primary blades,
wherein, when the primary blades are in the closed position, the contact area of the supplementary blade contacts the convex outer surface of at least one of the plurality of primary blades, such that a distal region of the supplementary blade lies close to or in contact with the primary blades when the primary blades are in the closed position, and
wherein the contact area between the supplementary blade and the primary blade moves from the distal region of the supplementary blade to a proximal region towards the anchor portion of the supplementary blade as the primary blades are opened, such that the proximal movement of the contact area drives the supplementary blade to splay laterally in a second direction perpendicular to the first direction of the opening movement of the primary blades and thereby moves the supplementary blade into the extended position in response to opening of the primary blades, and
wherein the at least one supplementary blade is resilient to return to a retracted position when the primary blades close, such that the distal region of the at least one supplementary blade lies close to or in contact with the convex outer surface of the primary blades.

2. The speculum of claim 1, wherein the at least one supplementary blade comprises at least one wing lying outside a plane containing the anchor portion.

3. The speculum of claim 1, wherein the at least one supplementary blade comprises a spine section extending from the anchor portion.

4. The speculum of claim 1, wherein the at least one supplementary blade comprises a continuously curved cross-section in a direction perpendicular to the longitudinal axis of the at least one supplementary blade.

5. The speculum of claim 1, wherein the at least one supplementary blade comprises a discontinuous cross section in a direction perpendicular to the longitudinal axis of the at least one supplementary blade interrupted by a crease.

6. The speculum of claim 1, wherein the at least one supplementary blade comprises a discontinuous cross section in a direction perpendicular to the longitudinal axis of the at least one supplementary blade interrupted by a plurality of parallel creases.

7. The speculum of claim 5, wherein the cross-section of the at least one supplementary blade comprises two or more generally flat portions extending from the crease.

8. The speculum of claim 1, wherein the at least one supplementary blade comprises a major portion tapering generally toward the distal end opposed to the anchor portion.

9. The speculum of claim 8, wherein the at least one supplementary blade comprises a minor portion tapering generally toward the anchor portion.

10. The speculum of claim 1, wherein the fastener comprises a fastening attachable to the speculum in two or more attachment positions.

11. The speculum of claim 10, wherein a first attachment position of the two or more attachment positions is laterally inward of a second attachment position.

12. The speculum of claim 1, wherein the fastener comprises a stud engageable within a hole in the speculum.

13. The speculum of claim 10, wherein the fastener comprises a stud engageable within a hole in the speculum and wherein the stud comprises a plurality of waists each defining a respective attachment position.

14. The speculum of claim 1, wherein a cross-section perpendicular to the longitudinal axis of the at least one supplementary blade comprises a spine and two wings lying to a same side of the spine.

15. The speculum of claim 14, wherein the cross-section perpendicular to the longitudinal axis of the at least one supplementary blade is symmetrical about a central longitudinal axis of the spine.

16. The speculum of claim 1, wherein said fastener is adapted to attach the at least one supplementary blade to the speculum in a releasable manner.

* * * * *